United States Patent [19]

Töpfl et al.

[11] Patent Number: 5,135,927
[45] Date of Patent: Aug. 4, 1992

[54] MICROBICIDAL COMPOSITION

[75] Inventors: Werner Töpfl, Dornach; Robert Nyfeler, Basel; Werner Föry, Riehen, all of Switzerland

[73] Assignee: Ciba-Geigy Corporation, Ardsley, N.Y.

[21] Appl. No.: 617,702

[22] Filed: Nov. 26, 1990

Related U.S. Application Data

[63] Continuation-in-part of Ser. No. 336,166, Apr. 11, 1989, Pat. No. 4,992,434, which is a continuation-in-part of Ser. No. 147,388, Jan. 25, 1988, abandoned.

[30] Foreign Application Priority Data

Jan. 30, 1987 [CH]  Switzerland .................... 351/87

[51] Int. Cl.$^5$ ............................. A01N 43/78
[52] U.S. Cl. .................. 514/212; 514/236.8; 514/326; 514/365; 548/200
[58] Field of Search ................ 548/200; 514/365, 326, 514/212, 236.8

[56] References Cited

U.S. PATENT DOCUMENTS

| | | | |
|---|---|---|---|
| 3,547,917 | 12/1970 | Kulka | 260/247 |
| 3,725,427 | 4/1973 | Harrison et al. | 260/302 |
| 4,199,506 | 4/1980 | Howe | 548/201 |
| 4,251,261 | 2/1981 | Howe et al. | 71/90 |
| 4,308,391 | 12/1981 | Howe et al. | 548/194 |
| 4,437,875 | 3/1984 | Howe et al. | 71/90 |
| 4,586,948 | 5/1986 | Howe et al. | 71/90 |
| 4,602,454 | 7/1986 | Howe et al. | 47/57.6 |
| 4,602,937 | 7/1986 | Howe et al. | 71/90 |
| 4,640,702 | 2/1987 | Grabiak et al. | 71/90 |

FOREIGN PATENT DOCUMENTS

| | | | |
|---|---|---|---|
| 44201 | 1/1982 | European Pat. Off. | 548/201 |
| 0279239 | 8/1988 | European Pat. Off. | |
| 0335831 | 10/1989 | European Pat. Off. | |
| 2020662 | 11/1979 | United Kingdom | |

OTHER PUBLICATIONS

Craig et al. Phytopathology, 77–1530 (1987).

*Primary Examiner*—Robert Gerstl
*Attorney, Agent, or Firm*—Marla J. Mathias; Edward McC. Roberts

[57] ABSTRACT

A microbicidal composition contains as active ingredient 2-chloro-4-trifluoromethylthiazol-5-carboxylic acid derivatives of the formula I

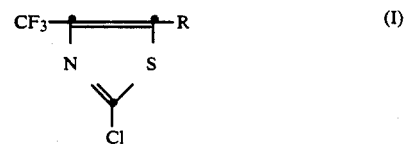

R is an organic radical with up to 40 carbon atoms, which optionally contains nitrogen, oxygen or sulfur atoms and which can be transformed by hydrolosis or oxydation into the directly to the thiazol ring bound carboxyl rest.

These compounds have good microbicidal activity and are used for the control and prevention of infestation of plants by phytophathogenic microorganisms.

10 Claims, No Drawings

MICROBICIDAL COMPOSITION

This is a continuation-in-part of application Ser. No. 366,166, filed Apr. 11, 1989, now U.S. Pat. No. 4,992,434, issued Feb. 12, 1991, which in turn is a continuation-in-part of application Ser. No. 147,388 filed Jan. 25, 1988, now abandoned.

The present invention relates to a microbicidal compositions which contain as active ingredient a 2-chloro-4-trifluoromethyl-thiazol-5-carboxylic acid derivative of formula I, to the preparation of these derivatives and to compositions containing them, as well as to methods for controlling or preventing infestation of plants by phytopathogenous microorganisms.

The 2-chloro-4-trifluoromethyl-thiazol-5-carboxylic acid derivatives correspond to the formula I

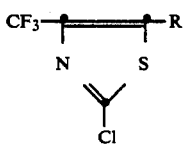

(I)

wherein R is an organic radical with up to 40 carbon atoms which optionally contains nitrogen, oxygen or sulfur atoms and which can be transformed by hydrolosis or oxydation into the directly to the thiazol ring bound carboxyl rest.

Thiazol-5-carboxylic acid derivatives are known from the literature. 2,4-Dimethylthiazol-5-carboxamides are disclosed as fungicides in U.S. Pat. No. 3,725,427; 2-chloro-4-trifluoromethylthiazol-5-carboxylic acid derivatives are disclosed as antidots (safeners) to reduce the phytotoxic action of strong herbicides on cultivated plants in U.S. Pat. Nos. 4,199,506, 4,251,261, 4,308,391, 4,437,875, 4,437,876 and 4,640,702 and in the published European patent applications 27,018, 44,201 and 63,353.

It has been found that the 2-chloro-4-trifluoromethyl-thiazol-5-carboxylic acid derivatives of formula I have extraordinary good microbicidal activity and are able to protect cultivated plants from infestation by phytopathological microbes and fungi or cure them of such infestation.

The compounds of formula I are stable at room temperature. They can be used in the agricultural sector or related fields for controlling pests, especially preventively and curatively for the control of phytopathogenic microorganisms. The derivatives of formula I are characterised by excellent fungicidal activity over a wide concentration range and by unproblematic handling. These derivatives further possess nematicidal properties which makes them suitable also for controlling nematodes, especially phytopathogenic nematodes.

By virtue of their pronounced microbicidal activity the derivatives of formula I are preferred, wherein the rest R contains a maximum of 25 carbon atoms, among them the derivatives falling under the formula Ia

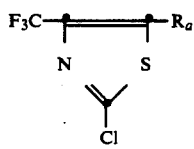

(Ia)

wherein $R_a$ is a radical selected from among cyano, —$COXR_1$, —$CONR_3R_4$ or —COD, X is oxygen or sulfur, $R_1$ is hydrogen; $C_1$-$C_{18}$alkyl, which is unsubstituted or substituted by halogen, a group cyano, nitro, —$YR_2$, A, —$N(R_3)COA$, —$[N(R_3)]_m$—$CON[(CO)_m$—$R_3$-$]_m$—$(CO)_mR_4$ in which group one of the indices m must be zero, —$C(X)_mXR_7$, —$(X)_m$—$CXA$, —PO $(R_5)R_6$, $C_3$-$C_8$cycloalkyl or $C_5$-$C_8$cycloalkenyl, which is unsubstituted or substituted by halogen, $C_1$-$C_4$alkyl or methylenedioxy; $R_1$ further represents $C_3$-$C_8$-alkenyl, $C_3$-$C_{18}$cycloalkyl or $C_3$-$C_{18}$cycloalkenyl, which is unsubstituted or substituted by halogen, $C_1$-$C_4$alkoxy, $C_1$-$C_4$alkylthio, $C_1$-$C_4$haloalkoxy, $C_1$-$C_4$haloalkyl, methylenedioxy or —$CO(O)_m$—$R_7$, —COA, or —$PO(R_5)R_6$; $R_1$ further represents $C_3$-$C_8$alkynyl which is unsubstituted or substituted by halogen or represents —$(E)_mU$ or —$(E)_mQ$, $R_2$ is $C_1$-$C_8$alkyl or $C_3$-$C_8$cycloalkyl, which is unsubstituted or substituted by $C_1$-$C_8$alkoxy, $C_1$-$C_8$alkylthio, $C_2$-$C_8$alkoxyalkyl halogen, cyano or —$CX(X)_mR_7$, —$(X)_m$—$CXA$, —$(X)_mCXR_7$, —$N(R_3)COA$, A, —X—U or XQ; $R_2$ further represents $C_3$-$C_8$alkenyl or $C_3$-$C_8$cycloalkenyl, which is unsubstituted or substituted by halogen or represents —$(E)_mU$ or —$(E)_mQ$;

m is zero or one;

Y is oxygen, sulfur, SO or $SO_2$;

A is a radical —$N(R_3)R_4$;

D is a radical —$N(R_3)N(R_4)(CO)_mR_3$;

$R_3$ and $R_4$ independently of each other represent hydrogen, $C_1$-$C_8$alkyl or $C_3$-$C_8$cycloalkyl, which is unsubstituted or substituted by $C_1$-$C_8$alkoxy, $C_2$-$C_8$alkoxyalkoxy, $C_1$-$C_8$alkylthio, cyano, —$COOR_{10}$, $C_1$-$C_4$alkylcarbamoyl, di-$C_1$-$C_4$alkylcarbamoyl, piperidinocarbonyl, pyrrolidinocarbonyl, piperidino or pyrrolidino; $R_3$ and $R_4$ further represent $C_3$-$C_8$alkenyl or $C_3$-$C_8$cycloalkenyl which is unsubstituted or substituted by halogen, $C_1$-$C_8$alkoxy, $C_3$-$C_8$cycloalkyl or cyano, —$COOR_7$, $C_1$-$C_4$alkylcarbamoyl, or piperidinocarbamoyl; $R_3$ and $R_4$ represent further $C_3$-$C_8$alkynyl which is unsubstituted or substituted by U, or $R_3$ and $R_4$ represent a radical —$(E)_mU$ or —$(E)_mQ$;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$-$C_8$alkoxy, amino, $C_1$-$C_4$-alkylamino di-$C_1$-$C_4$alkylamino or —$COOR_7$;

$R_5$ and $R_6$ are independently of each other are hydrogen or $C_1$-$C_4$alkoxy;

$R_7$ is hydrogen, $C_1$-$C_8$alkyl, $C_3$-$C_8$cycloalkyl, $C_3$-$C_8$alkenyl, $C_2$-$C_8$alkoxyalkyl, $C_3$-$C_8$alkoxyalkoxyalkyl, $C_1$-$C_4$haloalkyl, —$(C_1$-$C_3$alkylene)$_mU$, —$(C_1$-$C_3$alkylene)$_mQ$, $C_1$-$C_4$haloalkoxy;

U is phenyl or naphthyl, which is unsubstituted or substituted one to three times by halogen $C_1$-$C_4$alkyl, —Y—$C_1$-$C_4$alkyl, $C_1$-$C_4$haloalkyl, $C_1$-$C_4$haloalkoxy, cyano, nitro, carboxyl, —$COOR_7$, —$CONH_2$, —$CONHR_7$, —$CON(R_7)$, —$SO_2NHR_7$, —$SO_2N(R_7)_2$, pyrrolidino, piperidino, pyrrolidino, carbonyl or piperidinocarbonyl;

E is a $C_1$-$C_8$alkylene or $C_2$-$C_8$alkylene chain, which is unsubstituted or substituted by halogen, $C_1$-$C_4$alkoxy, $C_1$-$C_4$alkylthio, $C_1$-$C_4$haloalkoxy or by a rest —$CO(O)_mR_7$, —$(CO)_mA$, —$(CO)_mQ$ Q is a heterocycle which is bound via a carbon atom and is selected from among furan, tetrahydrofuran pyran, pentahydropyran, dioxolan, dioxan, benzdioxan, dihydrobenzdioxan, thienyl, thiazol, which may be substituted by halogen or methyl.

Good microbicidal activity show especially the derivatives of the formula Ib

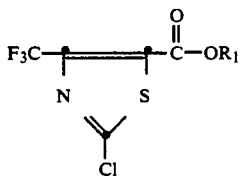

wherein $R_1$ has the meaning given above.

From U.S. Pat. Nos. 4,199,506, 4,251,261, 4,368,391, 4,437,875, and 4,437,876 are known the 2-chloro-5-trifluoromethyl-thiazol-5-carboxylic acid and derivatives wherein $R_1$ is hydrogen, an agriculturally acceptable salt, $C_1$-$C_{10}$alkyl, $C_1$-$C_{10}$haloalkyl, $C_2$-$C_{10}$alkoxyalkyl, $C_2$-$C_{10}$alkenyl, benzyl, phenyl and chlorophenyl. The other compounds encompassed by formula Ib are new, especially those wherein $R_1$ $C_1$-$C_{18}$ substituted by cyano, nitro, A, —$N(R_3)COA$, —$[N(R)_3]_m$—$CON[(CO)$-$_m$—$R_3]_m(CO)_mR_4$ wherein at least one of the indices m must be zero, —$C(X)_mXR_7$, —$(X)_mCXA$, $PO(R_3)R_6$, $C_1$-$C_8$cycloalkyl or $C_5$-$C_6$cycloalkenyl which is substituted by halogen, $C_1$-$C_4$alkyl or methylenedioxy; $R_1$ is further $C_3$-$C_{18}$cycloalkyl or $C_3$-$C_{18}$cycloalkenyl unsubstituted or $C_3$-$C_{18}$alkenyl, $C_3$-$C_{18}$cycloalkyl or $C_3$-$C_{18}$cycloalkenyl substituted by halogen, $C_1$-$C_4$alkoxy, $C_1$-$C_4$alkylthio, $C_1$-$C_4$haloalkoxy, $C_1$-$C_4$haloalkyl, methylenedioxy or —$CO(O)_mR_7$, —$COA$, or $PO(R_5)R_6$; $R_1$ is further $C_3$-$C_8$alkynyl which is unsubstituted or halogen substituted and $R_2$, m, Y, $R_3$, $R_4$, $R_5$, $R_6$ and $R_7$ have the meaning given above.

Also good activity is shown by the derivatives of the formula Ic

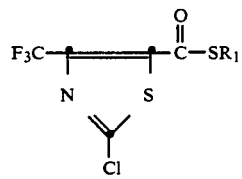

wherein $R_1$ is $C_1$-$C_{18}$alkyl or $C_3$-$C_{18}$cycloalkyl unsubstituted or $C_1$-$C_{18}$-alkyl substituted by halogen $C_1$-$C_8$alkoxy, $C_1$-$C_8$alkylthio, $C_2$-$C_8$alkoxyalkoxy nitro, cyano or A—, $CX(X)_mR_7$, —$N(R_3)COA$, A is —$N(R_3)R_4$ or —$(E)_mU$ m is zero or one $R_3$ and $R_4$ independently of each other are hydrogen, $C_1$-$C_8$alkyl, $C_3$-$C_8$-alkenyl or —$(E)_m$—U or $R_3$ and $R_4$ together with the nitrogen atom to which they are bound form a heterocycle selected from the group consisting of pyrrolidine, piperidine, azepine and morpholine $R_7$ is hydrogen or $C_1$-$C_{10}$alkyl E is $C_1$-$C_8$alkylene or $C_2$-$C_8$alkenylene chain U is phenyl or naphthyl, which is unsubstituted or substituted by halogen, $C_1$-$C_4$alkoxy or —$CO(O)_mR_7$, and X is oxygen or sulfur.

Compounds of the formula Ic, wherein $R_1$ is $C_1$-$C_3$alkyl, phenyl or benzyl are known from U.S. Pat. No. 4,640,702. The other compounds encompassed by formula Ic are new, especially those, wherein:

$R_1$ is $C_6$-$C_{18}$alkyl or $C_3$-$C_{18}$cycloalkyl unsubstituted or $C_1$-$C_{18}$alkyl or $C_3$-$C_{18}$cycloalkyl substituted by halogen, $C_1$-$C_8$alkoxy, $C_1$-$C_8$alkylthio, $C_2$-$C_8$alkoxyalkoxy, nitro, cyano or A—, $CX(X)_mR_7$, —$N(R_3)COA$, A is —$N(R_3)R_4$ m is zero or one $R_3$ and $R_4$ independently of each other one hydrogen, $C_1$-$C_8$alkyl, $C_3$-$C_8$-alkenyl or —$(E)_mU$. $R_3$ and $R_4$ together with the nitrogen atom, to which they are bound form a heterocycle selected from the group consisting of pyrrolidine, piperidine, azepine and morpholine $R_7$ is hydrogen or $C_1$-$C_{10}$alkyl E is a $C_1$-$C_8$alkylene or $C_2$-$C_8$alkenylene chain U is phenyl or naphthyl, which is unsubstituted or substituted by halogen, $C_1$-$C_4$alkoxy or —$CO(O)_mR_7$ and X is oxygen or sulfur.

Good microbicidal activity is found with compounds of formula Id

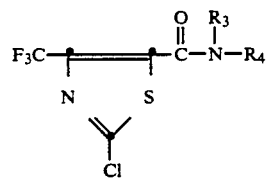

wherein $R_3$ and $R_4$ independently of each other represent hydrogen, $C_1$-$C_8$alkyl or $C_3$-$C_8$cycloalkyl, which is unsubstituted or substituted by $C_1$-$C_8$alkoxy, $C_2$-$C_8$alkoxyalkoxy, $C_1$-$C_8$alkylthio, cyano, —$COOR_7$, $C_1$-$C_4$alkylcarbamoyl, di-$C_1$-$C_4$alkylcarbamoyl, piperidinocarbonyl, pyrrolidinocarbonyl, piperidino or pyrrolidino; $R_3$ and $R_4$ further represent $C_3$-$C_8$alkenyl or $C_3$-$C_8$cycloalkenyl which is unsubstituted or substituted by halogen, $C_1$-$C_8$alkoxy, $C_3$-$C_8$cycloalkyl or a rest cyano, —$COOR_{10}$, $C_1$-$C_4$alkylcarbamoyl or piperidinocarbamoyl; $R_3$ and $R_4$ represent further $C_3$-$C_8$-alkynyl, which is unsubstituted or substituted by U, or $R_3$ or $R_4$ represent a radical —$(E)_m$—U or —$(E)$-$_m$—Q;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$-$C_8$alkoxy, amino, $C_1$-$C_4$-alkylamino di-$C_1$-$C_4$alkylamino, —$COOR_7$, $R_7$ is hydrogen, $C_1$-$C_8$alkyl, $C_3$-$C_8$cycloalkyl, $C_3$-$C_8$alkenyl, $C_2$-$C_8$alkoxyalkyl, $C_3$-$C_8$alkoxyalkoxyalkyl, $C_1$-$C_4$haloalkyl, —$(C_1$-$C_3$alkylene)$_m$U, —$(C_1$-$C_3$alkylene)$_m$Q, $C_1$-$C_4$haloalkoxy;

U is phenyl or naphthyl, which is unsubstituted or substituted one to three times by halogen, $C_1$-$C_4$alkyl, —Y—$C_1$-$C_4$alkyl, $C_1$-$C_4$haloalkyl, $C_1$-$C_4$haloalkoxy, cyano, nitro, —$COOR_7$, —$CONH_2$,—$CONHR_7$, —$CONR_7$, —$SOR_2NHR_7$, —$SO_2N(R_7)_2$, pyrrolidino, piperidino, pyrrolidino carbonyl or piperidinocarbonyl;

E is a $C_1$-$C_8$alkylene or $C_2$-$C_8$alkylene chain, which is unsubstituted or substituted by halogen, $C_1$-$C_4$alkoxy, $C_1$–$C_4$alkylthio, $C_1$–$C_4$haloalkoxy or by a rest —$CO(O)_mR_{10}$, —$(CO)_mA$, —$(CO)_mQ$ Q is a heterocycle which is bound via a carbon atom and is selected from among furan, tetrahydrofuran pyran, pentahydropyran, dioxolan, dioxan, benzdioxan, dihydrobenzdioxan, thienyl, thiazol, which may be substituted by halogen or methyl and Y is oxygen sulfur —SO or $SO_2$, especially the compounds 3-chloro-5-[N-(1-cyano-1-methylethyl)-N-methylamido]-4-trifluoromethylthiazol, 3-chloro-5-[N-(1-cyano-cyclohex-1-yl)-N-methylamido]-4-trifluoromethylthiazol, 3-chloro-5-[N-(1-cyano-cyclopent-1-yl)-N-methylamido]-4-trifluoromethylthiazol, 3-chloro-5-(furyl-2-amido)-4-trifluoromethylthiazol, 3-chloro-5-(phenyl-eth-1-ylamido)-4-trifluoromethylthiazol N,N-Diethyl-2-chloro-4-trifluoromethylthiazol-5-carboxamide is known from U.S. Pat. Nos. 4,199,506, 4,437,875, 4,437,876. The other compounds encompassed by formula Id are new. U.S. Pat. No. 3,725,427 discloses 2,4-dimethyl-thiazol-5-carboxamides with fungicidal activity. The compounds of formula Id show improved fungicidal activity over a wider application range.

Excellent microbicidal activity is further shown by the compounds corresponding to the formula Ie

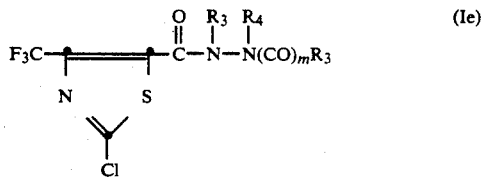

wherein m is 0 or 1 and $R_3$ and $R_4$ independently of each other are hydrogen, $C_1$–$C_8$alkyl or $C_3$–$C_8$cycloalkyl which is unsubstituted or substituted by $C_1$–$C_8$alkoxy, $C_2$–$C_8$alkoxyalkoxy, $C_1$–$C_8$alkylthio, cyano or —$COOR_7$, $C_1$–$C_4$alkylcarbamoyl or di-$C_1$–$C_4$alkylcarbamoyl or —$(E)_mU$; $R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine $R_7$ is hydrogen or $C_1$–$C_8$alkyl E is $C_1$–$C_8$alkylene or $C_2$–$C_8$alkenylene and U is phenyl or naphthyl, which is unsubstituted or substituted one to three times by halogen, $C_1$–$C_4$alkyl, —Y—$C_1$–$C_4$alkyl, $C_1$–$C_4$haloalkyl, $C_1$–$C_4$haloalkoxy, cyano, nitro, —$COOR_7$, —$CONH(R_7)$, $SO_2NHR_7$ or $SO_2N(R_7)_2$ and Y is oxygen, sulfur, SO or $SO_2$, especially 5-(benzoylhydrazinocarbonyl)-3-chloro-4-trifluoromethyl-thiazol and 3-chloro-5-(2,4,6-trichlorobenzoylhydrazinocarbonyl)-4-trifluoromethylthiazol.

In these definitions, the alkyl radicals, were not otherwise specified, are understood to have 1 to 18 carbon atoms. They can be straight-chain or branched. The most common radicals are e.g. methyl, ethyl, n-propyl, isopropyl, n-butyl, isobutyl, sec.butyl, tert.butyl, n-pentyl, isopentyl, n-hexyl and n-octyl. The alkenyl and alkynyl radicals can also be straight-chain or branched and contain 3 to 18 carbon atoms. The most commonly used radicals are e.g. allyl, methallyl, butene butadiene. propynyl, methylpropynyl, 1-butynyl and 2-butynyl, Cycloalkyl or cycloalkenyl radicals have preferably 3 to 13 carbon atoms and can also be benzannellated.

Typical representatives are e.g. cyclopropyl, cyclopentyl, cyclohexyl, cyclohexenyl, idan, tetrahydronaphthalin, decalin. Halogen stands for fluorine, chlorine, bromine and iodine atoms, especially fluorine and chlorine. Haloalkyl and haloalkenyl radicals are mono- or polysubstituted with halogen atoms.

The above-mentioned radicals may be unsubstituted or substituted, typical substituents of these radicals are e.g. halogen or alkyl, alkenyl, alkynyl, cycloalkyl, aryl or aralkyl radicals that are bound by way of oxygen, sulfur or an imino group. The aryl radicals may be substituted in turn. They may also be bound by may of a sulfinyl-, sulfonyl-, carbonyl-, carbonyloxy-, carbamoyl-, sulfamoyl- or an amino-oxy-bridge to the alicyclic hydrocarbon.

The substituent Q, and also the radicals $R_3$ and $R_4$ with the nitrogen atom, to which they are bound may form an unsaturated or saturated heterocycle with 5 to 12 ring members, which may include one two or three additional heteroatoms or a sulfinyl- or sulfonyl group. They can further contain one or two carbonyl groups and be benzoannellated unsubstituted or substituted.

Suitable heteroatoms are in this context one, two or three additional nitrogen atoms, up to two oxygen or sulfur atoms, which cannot be in vicinal position.

Examples for such heterocycles are listed below: pyrroline, pyrrolidine, imidazoline, imidazolidine, pyrazoline, pyrazolidine, isazoline, isazolidine, oxazoline, oxazolidine, isothiazolidine, thiazoline, thiazolidine, diathiazolidine, oxadiazolidine, piperidine, piperazine, tetrahydropyrimidine and pyrazine, morpholine, thiomorpholine, thiazine, hexahydrotriazine, tetrahydropyrazine, oxadiazine, oxatriazine, hexahydroazepine, hexahydrodiazepine, diazepine, hexahydrodiazepine, azacyclooctan, indoline, isoindoline, benzimidazoline, benzindazoline, benzoxazoline, benzthiazoline, benzisooxazoline, benzthiazole, tetrahydrochinoline, tetrahydroisochinoline, tetrahydrochinazoline, tetrahydrochinoxzline, tetrahydrophthalazine, bemzomorpholine, benzothiomorpholine, tetrahydrobenzazepine, tetrahydrobenzidiazepine, tetrahydrobenzoxazepine, 1,5-diabicycle[4.3.0]nonane, dihydrobenzoxazepine, 1,6-diabicyclo[5.3.0]decane, 1,4-diabicyclo[3.3.0]octane, 1,5-diazabicyclo[4.4.0]decane.

The above heterocycles can also be substituents. Further examples of heterocyclic systems which may occur as substituents are e.g. pyrrole, imidazole, pyrazole, isoxazole, thiazole, triazole, oxadiazole, thiadiazole, tetrazole, oxatriazole, thiatriazole, furan, tetrahydrofuran, dioxole, dioxolane, oxathiole, oxathiolane, thiophen, tetrahydrothiophen, dithiolan, dithiazole, pyridine, pyran, thiopyran, pyridazine, pyrimidine, pyrazine, tetrahydropyran, tetrahydrothiopyran, dioxin, dioxan, dithiin, dithian, oxazine, thiazine, oxathiine, oxzthiane, triazine, oxadiazine, thiadiazine, oxathiazine, dioxazine, azepine, oxepin, thiepin, diazepine, oxazepine, indole, benzofuran, benzothiophen, indazole, benzimidazole, benzidioxol, benzdithiol, benzisoxazole, benzthiazole, benzoxazle, benzoxzthiole, benztriazole, benzoxadiazole, benzofurazane, benzothiadiazole, quinolin, isoquinolin, chromene, chromane, isochromene, isochromane, thiochromene, isothiochromene, thiochromane, isothiochromane, cinnoline, chinazoline, chinoxaline, phtalazine, benzidioxin, benzdithiin, benzoxazine, benzdioxan, benzoxathiane, benzotriazine, benzazepine, benzdilazepine, benzoxazepine, purine, pteridine, phenoxazine, phenothiazine.

The heterocyclic radicals can be substituted as mentioned above.

Some derivatives of the formula I are known from the literature and can be produced by known methods.

The thiazol derivatives of formula I are produced e.g. according to U.S. Pat. No. 4,199,506, by condensing an acrylic acid ester of the formula II with chlorocarbonyl-sulfonylchloride of the formula III, according to the reaction scheme

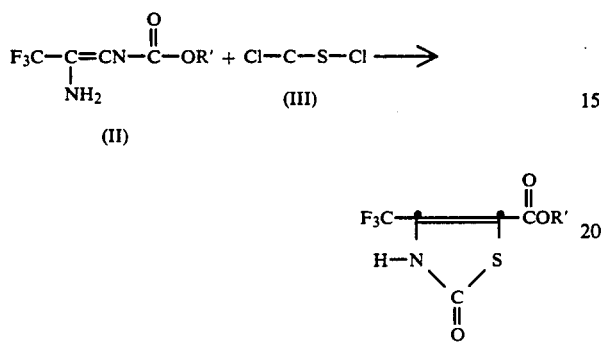

The resulting 2-oxo-4-trifluoromethyl-thiazol-5-carboxylic acid derivative is treated with phosphoroxychloride whereby according to the reaction conditions and the amount of phoshoroxychloride used, a 2-chloro-4-trifluoromethyl-thiazol-5-carboxylic acid derivative of the formula Ia or 2-chloro-4-trifluoromethyl-thiazol-carbochloride of the formula IIa

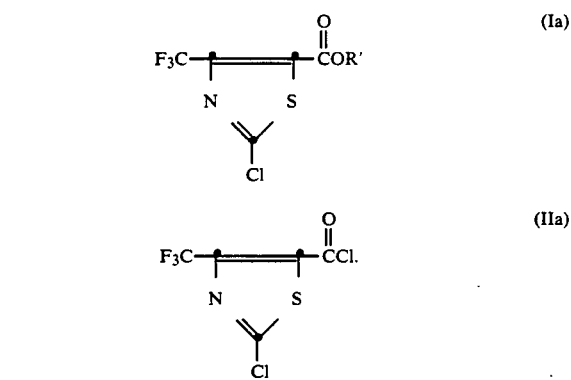

Acrylic acid derivatives of the formula III can be prepared according to J. Het. Chem. 9 (1972) S13 by condensing an acetoacetic ester with trifluoromethylnitril in a boiling solvent in the presence of sodium acetate, according to the reaction scheme

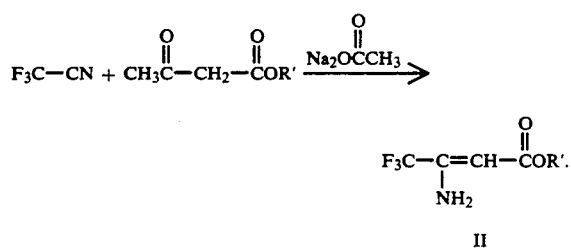

Using 2-chloro-4-trifluoromethyl-thiazol-5-carbochloride of formula IIa, the following active derivatives of formula I can be prepared according to known methods:

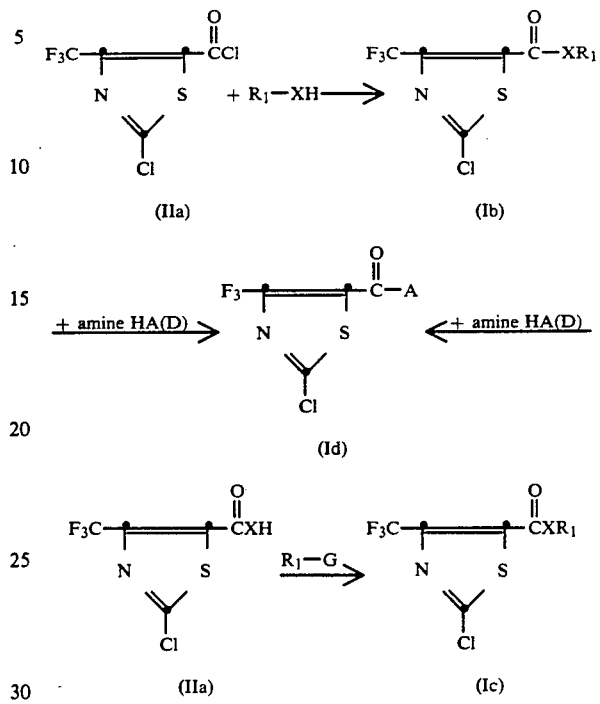

In these formulae A and $R_1$ have the meaning given above under formula Ia and G is an instable nucleofugal rest, such as a halogen atom or a lower-alkyl sulfoxy rest.

In these reactions inert solvents and diluents are used to suit the particular reaction conditions. The following may be mentioned as examples: halohydrocarbons, especially chlorohydrocarbons, such as tetrachloroethylene, tetrachloroethane, dichloropropane, methylene chloride, dichlorobutane, chloroform, chloronaphthalene, dichloroanaphthalene, carbon tetrachloride, trichloroethane, trichloroethylene, pentachloroethane, difluorobenzene, 1,2-dichloroethane, 1,1-dichloroethane, 1,2-cis-dichloroethylene, chlorobenzene, fluorobenzene, bromobenzene, iodobenzene, dichlorobenzene, dibromobenzene, chlorotoluene and trichlorobenzene; ethers, such as ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxan, thioanisole and dichlorodiethyl ether; nitrohydrocarbons, such as nitromethane, nitroethane, nitrobenzene, chloronitrobenzene and o-nitrotoluene; nitriles, such as acetonitrile, butyronitrile, isobutyronitrile, benzonitrile and m-chlorobenzonitrile; aliphatic or cycloaliphatic hydrocarbons, such as heptane, pinane, nonane, cymol, petroleum fractions within a boiling range of from 70° to 190° C., cyclohexane, methylcyclohexane, Decalin, petroleum ether, hexane, ligroin, trimethylpentane, 2,3,3-trimethylpentane and octane; esters, such as ethyl acetate, ethyl acetoacetate and isobutyl acetate; amides, for example formamide, methylformamide and dimethylformamide.

Surprisingly, it has been found that compositions containing the compounds of formula I as active ingredient have, for practical field application purposes, a very advantageous microbicidal spectrum against phytopathogenic fungi and bacteria. Compounds of formula I have very advantageous curative, systemic and, in particular, preventive properties, and can be used for protecting numerous cultivated plants, With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Fungi imperfecti (e.g. Botrytis, Helminthosporium, Fusarium, Septoria, Cercospora, Pyricularia, Alternaria); Basidiomycetes (e.g. the genera Hemileia, Rhizocotonia, Puccinia); and, in particular, against the class of Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings aginst fungus infections as well as against phytopathogenic fungi which occur in the soil.

Apart from their microbicidal activity, the compounds of formula I have nematocidal properties which, in particular, makes them suitable for controlling plant nematodes, For this utility, the compositions of the invention can be used curatively, preventively or systemically. They exhibit a broad range of activity against the various species of nematode and therefore satisfy the requirements of practice.

In the rates of application indicated below, the compounds of the invention, are especially well tolerated by plants.

Accordingly, the invention also relates to microbicidal compositions as well as to the use of the compounds of formula I for controlling phytopathogenic microorganisms, in particular phytopathogenic fungi, or for protecting plants from attack by said microorganisms.

The invention further embraces the preparation of agrochemical compositions, which comprises homogeneously mixing the active ingredient with one or more compounds or groups of compounds described herein. The invention furthermore relates to a method of treating plants, which comprises applying thereto the compounds of formula I or the novel compositions.

Target crops to be protected with the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This recitation constitutes no limitation.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, which can be obtained e.g. from animal or plant cells, in particular from soybeans.

Examples of useful physical forms are phosphatidyl choline mixtures. Examples of synthetic phospholipids are dioctanoylphosphatidyl choline and dipalmitoylphosphatidyl choline.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 8 carbon atoms in the alkyl moiety of the alkylphenols.

Further suitable non-ionic surfactants are the water-soluble adducts of polyethylene oxide with polypropylene glycol, ethylenediamino-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. sterayltrimethylammonium chloride or benzyldi(2-chloroethyl)ethylammonium bromide.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions constitute an object of the present invention.

The following non-limitative Examples serve to illustrate the invention in more detail. Temperatures are given in Centigrades in the following examples and tables, pressures are given in millibar (mbar), percentages and parts are by weight.

EXAMPLE 1.1

Preparation of 2-chloro-5-(2-phenoxyethoxycarbonyl)-4-trifluoromethyl-thiazole

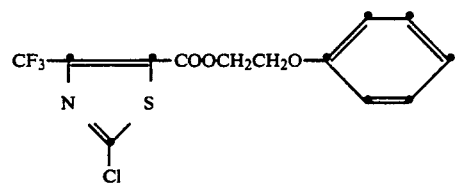

6.3 g (0.045 mol) of 2-phenoxyethanol are added slowly while stirring to a solution of 11 g (0.44 mol) of 2-chloro-5-chlorcarbonyl-4-trifluoromethyl-thiazole in 100 ml of absolute toluene. The solution is then cooled to 0°-5° and 3.6 g (0.045 mol) of triethylamine are added dropwise while stirring. Triethylamine-hydrochloride precipitates from the reaction mixture. After everything is added, the suspension is stirred for 20 hours at room temperature and then poured onto ice-water. The organic phase is separated, dried over sodium sulfate and concentrated in a rotatory evaporator. The residue cristallizes. In order to purify it, the crystals are suspended in petrol-ether, filtered and dried. In this manner 8.7 g (57% of the theoreticl yield) of the title compound are obtained, m.p. 70°-72°.

EXAMPLE 1.2

Preparation of 2-chloro-5-(N-benzyl-N-isopropylamido)-4-trifluoromethyl-thiazole

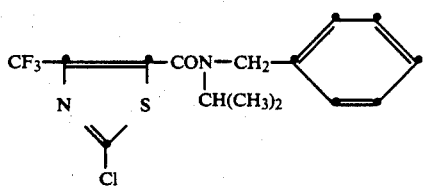

A solution of 2.8 g (0.027 mol) of triethylamine and 4.1 g (0.027 mol) of N-isopropylbenzylamine in 50 ml of ethylacetate are added dropwise at 0° to 5° into a stirred solution of 6.5 g (0.025 mol) of 2-chloro-3-chlorocarbonyl-4-trifluoromethyl-thiazole. After the addition is complete, the reaction mixture, which has turned into a yellow solution is stirred for 15 hours at room temperature and then poured onto ice-water. The organic phase is separated, dried over sodium sulfate, purified with active charcoal, filtered and concentrated on a rotatory evaporator. The residue, a red-brown oil is purified by chromatography in ethyl acetate/hexan over a silica-gel column. After evaporation of the eluant, there remains 6.5 g (73% of the theoretical yield) of a colourless oil with correct chemical analysis.

EXAMPLE 1.3

Preparation of 2-chloro-5-(1-methoxycarbonyl-eth-1'-yloxycarbonyl)-4-trifluoromethyl-thiazole

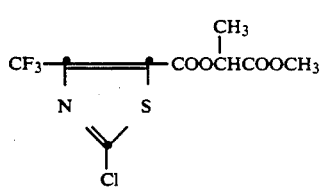

A mixture consisting of 6.94 g of 2-chloro-5-carboxyl-4-trifluoromethyl-thiazole, 5 g of 2-bromopropionic acid-methyl ester and 4.5 g of potassium carbonate, suspended in 50 ml of anhydrous dimethylformamide is stirred under nitrogen atmosphere at room temperature during 3 hours. The reaction-mixture is then filtered and the filtrate is poured into ice-water/ethyl-acetate 1:1. The organic phase is separated, washed 3 times with ice-water, dried and concentrated in a rotatory evaporator. The residue, a colourless oil is distilled for purification. One obtains 8.5 g (75% of the theoretical yield) of title product as colourless oil b.p. 75°-80°/0.015 mbar.

In analogy to these examples the following compounds are prepared:

TABLE 1

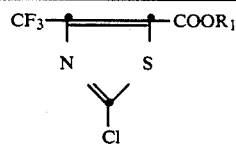

(Ib)

| No. | $R_1$ | phys. constant |
|---|---|---|
| 1.001 | 1-dodecyl | |
| 1.002 | 1-octadecyl | |
| 1.003 | cyclopropylmethyl | |
| 1.004 | cyclopentylmethyl | |
| 1.005 | cyclohexylmethyl | |
| 1.006 | cyclohexylethyl | |
| 1.007 | tetrahydrofuran-2-yl-methyl | |
| 1.008 | pentahydropyran-2-yl-methyl | m.p. 60–63° |
| 1.009 | 2,2-dimethyl-1,3-dioxolan-4-yl-methyl | oil |
| 1.010 | 1,2-dihydrobenz-1,4-dioxan-2-ylmethyl | resin |
| 1.011 | furan-2-ylmethyl | |
| 1.012 | thiophen-2-ylmethyl | oil |
| 1.013 | 3,4-methylendioxybenzyl | m.p. 96–98° |
| 1.014 | thiophen-2-ethyl | |
| 1.015 | 5-methyl-thiazol-4-yläthyl | m.p. 64–67° |
| 1.016 | phenylethyl | |
| 1.017 | para tolyl-eth-1-yl | oil |
| 1.018 | 3,45-trimethoxybenzyl | |
| 1.019 | geranyl | |
| 1.020 | 2-hexen-1-yl | |
| 1.021 | 1-hexen-6-yl | |
| 1.022 | 1-hexen-3-yl | |
| 1.023 | 2-chloro-2-propen-1-yl | |
| 1.024 | 3-chloro-2-propen-1-yl | |
| 1.025 | 3-phenyl-2-propen-1-yl | |
| 1.026 | cyclopentyl | |
| 1.027 | cyclohexyl | |
| 1.028 | 2-methyl-cyclohexyl | |
| 1.029 | 3-methyl-cyclohexyl | |
| 1.030 | 4-methyl-cyclohexyl | |
| 1.031 | cyclododecyl | |
| 1.032 | 2,3-dimethyl-cyclohexyl | |
| 1.033 | 2,4-dimethyl-cyclohexyl | |
| 1.034 | 2,6-dimethyl-cyclohexyl | |
| 1.035 | 3,5-dimethyl-cyclohexyl | |
| 1.036 | 4-tert.butyl-cyclohexyl | |
| 1.037 | bornyl | m.p. 65–67° |
| 1.038 | norbornyl | oil |
| 1.039 | fenchyl | oil |
| 1.040 | menthyl | oil |
| 1.041 | 2,2-dichlor-cyclopropylmethyl | |
| 1.042 | —$CH_2$—CN | |
| 1.043 | —$CH_2$—$CH_2$—CN | oil |
| 1.044 | —$CH_2$—PO(O$C_2H_5$)$_2$ | |
| 1.045 | 2-nitro-ethyl | |
| 1.046 | 2-allyloxy-ethyl | |
| 1.047 | 2-benzyloxy-ethyl | |
| 1.048 | para-chlorbenzyloxyethyl | |
| 1.049 | ortho-chlorbenzyloxyethyl | |
| 1.050 | cyclopropyloxyethyl | |
| 1.051 | cyclohexyloxyethyl | |
| 1.052 | 2-phenoxyethyl | m.p. 70–72° |
| 1.053 | para-chlorphenoxyethyl | |
| 1.054 | —$CH_2$—$CH_2$—S$CH_3$ | |
| 1.055 | —$CH_2$—$CH_2$—SO—$CH_3$ | |
| 1.056 | —$CH_2$—$CH_2$—$SO_2$—$CH_3$ | m.p. 86–88° |
| 1.057 | —$CH_2$—$CH_2$—$CH_2$—S$CH_3$ | |
| 1.058 | —$CH_2$—$CH_2$—$CH_2$—SO—$CH_3$ | |
| 1.059 | —$CH_2$—$CH_2$—$CH_2$—$SO_2$—$CH_3$ | |
| 1.060 | —$CH_2$—$CH_2$—S—$C_4H_9$(n) | |
| 1.061 | —$CH_2$—$CH_2$—S—$CH_2$—CH=$CH_2$ | |
| 1.062 | cyclohexylthioethyl | |
| 1.063 | benzylthioethyl | |
| 1.064 | para-chlorbenzylthioethyl | |
| 1.065 | phenylthioethyl | m.p. 47–49° |
| 1.066 | phenylsulfonylethyl | |
| 1.067 | para-tolylthioethyl | |
| 1.068 | para-chlorphenylthioethyl | |
| 1.069 | phenylthiopropyl | |
| 1.070 | β-naphthylthioethyl | |
| 1.071 | 2-phenylthio-1-methyl-ethyl | |
| 1.072 | 2-phenylthio-1-chloromethyl-ethyl | |
| 1.073 | —$CH_2$—$CH_2$—S—$CH_2$—COO$C_2H_5$ | |

TABLE 1-continued

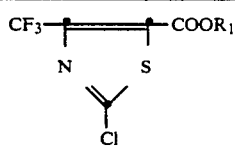 (Ib)

| No. | R₁ | phys. constant |
|---|---|---|
| 1.074 | —CH₂CH₂SCH(CH₃)COOC₂H₅ | |
| 1.075 | —CH₂—CH₂—S—CO—N(CH₃)₂ | |
| 1.076 | piperidinoylthioethyl | |
| 1.077 | —CH₂—CH₂—S—CS—N(CH₃)₂ | |
| 1.078 | piperidinothiocarbonylthioethyl | |
| 1.079 | —CH₂—COOCH₃ | |
| 1.080 | —CH₂—COOC₂H₅ | b.p. 80–85°/ 0.025 mbar |
| 1.081 | —CH₂—COOC₄H₉(n) | |
| 1.082 | —CH(CH₃)COOCH₃ | b.p. 25–80°/ 0.015 mbar |
| 1.083 | —C(CH₃)₂COOC₂H₅ | |
| 1.084 | —CH₂—CH₂—COOC₂H₅ | |
| 1.085 | 5,5-dimethyl-tetrahydrofuran-2-on-3-yl | m.p. 100–102° |
| 1.086 | —CH₂—CO—N(C₂H₅)₂ | |
| 1.087 | —CH₂CON[CH(CH₃)₂]₂ | |
| 1.088 | —CH₂CON[CH₂(CH₃)C₂H₅]₂ | |
| 1.089 | —CH₂CON[CH₂CH=CH₂)₂ | |
| 1.090 | 2-methylpiperidinoylmethyl | |
| 1.091 | azepinoylmethyl | oil |
| 1.092 | anilidomethyl | |
| 1.093 | N-methyl-anilidomethyl | |
| 1.094 | N-(2,6-dimethylphenyl)-N-(methoxy-carbonyl-eth-1-yl)-carbamoylmethyl | m.p. 95–97° |
| 1.095 | 1-(piperidinocarbonyl)-eth-1-yl | m.p. 62–66° |
| 1.096 | —CH₂—CH₂—NH—CO—CH₃ | |
| 1.097 | cyclopropancarbamoyl-ethyl | |
| 1.098 | —CH₂—CH₂—NH—CO—CH₂—Cl | |
| 1.099 | —CH₂—CH₂—NH—CO—CHCl₂ | |
| 1.100 | benzamoyl-ethyl | |
| 1.101 | thienyl-2-carbamoylethyl | |
| 1.102 | furylcarbamoylethyl | |
| 1.103 | —CH₂—CH₂—NH—CO—NH—CH₃ | |
| 1.104 | C(CH₃)₃ | |
| 1.105 | phenylureylene-ethyl | |
| 1.106 | —CH₂CH₂N(CH₃)COCH₃ | |
| 1.107 | —CH₂CH₂N(CH₃)COCHCl₂ | |
| 1.108 | —CH₂CH₂N(CH₃)CONHCH₃ | |
| 1.109 | —CH₂CH₂N(CH₂)SO₂CH₃ | |
| 1.110 | N-methyl-phenylsulfamoyl-ethyl | |
| 1.111 | —CH₂CH₂N(C₃H₇-i)COCHCl₂ | |
| 1.112 | —CH₂CH₂N(CH₂CH=CH₂)CONHCl₂ | |
| 1.113 | 2-oxo-pyrrolidino-ethyl | m.p. 58–62° |
| 1.114 | dicyclohexylmethyl | |
| 1.115 | α-phenylbenzyl | oil |
| 1.116 | α-methylbenzyl | |
| 1.117 | α-carboxylbenzyl | |
| 1.118 | α-carboxyl-para-chlorbenzyl | |
| 1.119 | α-methoxycarbonyl-benzyl | m.p. 62–64° |
| 1.120 | α-ethoxycarbonyl-benzyl | |
| 1.121 | α-cyanobenzyl | m.p. 78–81° |
| 1.122 | α-benzoyl-benzyl | m.p. 105–109° |
| 1.123 | α-methoxycarbonyl-α-phenylbenzyl | m.p. 106–110° |
| 1.124 | —CH₂—CH₂—N(CH₃)₂ | |
| 1.125 | pyrrolidinoethyl | |
| 1.126 | piperidinoethyl | |
| 1.127 | morpholinoethyl | m.p. 185–187° (hydrochloride) |
| 1.128 | anilinoethyl | |
| 1.129 | para(1-methoxycarbonyl)ethoxyphenyl | |

TABLE 1-continued

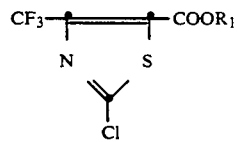 (Ib)

| No. | R₁ | phys. constant |
|---|---|---|
| 1.130 | para(3-methyl-1,3-oxazolidin-2-yl)phenyl | |
| 1.131 | para(N'N'-(dimethyl-ureylene)-phenyl | |
| 1.132 | meta(N',N'-dimethyl-ureylene)phenyl | |
| 1.133 | β-cyano-β-methoxycarbonyl-styryl-4-yl | |
| 1.134 | β,β-di(methoxycarbonyl)-styryl-4-yl | |
| 1.135 | β,β-dicyano-styryl-4-yl | |
| 1.136 | C₂H₅ | m.p. 59–60° |
| 1.137 | H | m.p. 122–125° |
| 1.138 | benzyl | m.p. 56–58° |
| 1.139 | (4,4-dimethyl-tetrahydro-fur-3-yl-2-on) | m.p. 100–102° |
| 1.140 | (4-methyl-thiazol-5-ylethyl) | m.p. 64–67° |
| 1.141 | (2,3,5,6-diepoxy-cyclo-hexan-1-yl) syn. isomer | m.p. 144–175° |
| 1.142 | (2,3,5,6-diepoxy-cyclo-hexan-1-yl) anti isomer | m.p. 144–120° |
| 1.143 | α-(4-chlorphenyl)benzyl | |
| 1.144 | α-(2-chlorphenyl)benzyl | |
| 1.145 | α-(4-chlorphenyl)-4-chlorbenzyl | |
| 1.146 | α-(2-chlorphenyl)-2-chlorbenzyl | |
| 1.147 | α-(2-chlorphenyl)-4-chlorbenzyl | |
| 1.148 | α-(4-flurophenyl)-benzyl | |
| 1.149 | α-(2-fluorphenyl)-benzyl | |
| 1.150 | α-(4-fluorphenyl)-4-fluorbenzyl | |
| 1.151 | α-(2-fluorphenyl)-2-fluorbenzyl | |
| 1.152 | α-(2-fluorphenyl)-4-fluorbenzyl | |
| 1.153 | α-(4-tolyl)-benzyl | |
| 1.154 | α-(4-anisyl)-benzyl | |
| 1.155 | α-(4-methoxyphenyl)-benzyl | |
| 1.156 | α-(3-trifluorphenyl)-benzyl | |
| 1.157 | 2-phenoxyethyl | |
| 1.158 | 2-2-dimethyl-1,3-dioxolon-2-ylmethyl | |
| 1.159 | 2-piperidinocarbonylethyl | |

TABLE 2

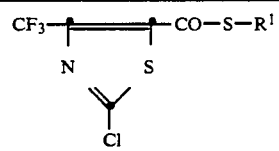 (Ic)

| No. | R₂ | phys. constant |
|---|---|---|
| 2.001 | —CH₂—COOH | |
| 2.002 | —CH₂—COOCH₃ | |
| 2.003 | —CH₂—COOC₂H₅ | |
| 2.004 | —CH(CH₃)COOH | |
| 2.005 | CH(CH₃)COOC₂H₅ | |
| 2.006 | —CH₂—CH₂—COOH | |
| 2.007 | —CH₂—CO—N(C₂H₅)₂ | |
| 2.008 | piperidinamoylmethyl | |
| 2.009 | azepinamoylmethyl | |
| 2.010 | anilidomethyl | |
| 2.011 | para chloranilidmethyl | |
| 2.012 | 2-carboxylphenylmethyl | |
| 2.013 | benzyl | m.p. 60–62° |

TABLE 3

$$\text{CF}_3-\overset{\underset{\displaystyle\underset{\text{Cl}}{\diagdown\diagup}}{\underset{\text{N}\qquad\text{S}}{\diagdown\diagup}}}{=}-\text{CO}-\text{N}\overset{R^3}{\underset{R^4}{\diagdown}}\qquad\text{(Id)}$$

| No. | R₃ | R₄ | phys. constant |
|---|---|---|---|
| 3.001 | allyl | allyl | |
| 3.002 | allyl | 2-methoxy-ethyl | |
| 3.003 | allyl | isopropyl | |
| 3.004 | 2-methyl-2-propen-1-yl | isopropyl | |
| 3.005 | 2-methyl-2-propen-1-yl | cyclohexyl | |
| 3.006 | 2-chlor-2-propen-1-yl | 2-methoxy-ethyl | |
| 3.007 | 2-chlor-2-propen-1-yl | isopropyl | |
| 3.008 | 2-chlor-2-propen-1-yl | cyclohexyl | |
| 3.009 | 2-chlor-2-propen-1-yl | 2-chlor-2-propen-1-yl | |
| 3.010 | 3-chlor-2-propen-1-yl | propyl | |
| 3.011 | propyl | 2-methoxy-ethyl | |
| 3.012 | methyl | cyclohexyl | |
| 3.013 | methyl | benzyl | |
| 3.014 | methyl | 2,6-dichlor-benzyl | m.p. 118–120° |
| 3.015 | isopropyl | benzyl | oil |
| 3.016 | isopropyl | 4-chlor-benzyl | |
| 3.017 | H | benzyl | |
| 3.018 | H | phenyl | |
| 3.019 | methyl | phenyl | |
| 3.020 | methyl | 4-chlor-phenyl | |
| 3.021 | ethyl | 2-chlor-4-brom-phenyl | |
| 3.022 | ethyl | 3-trifluormethyl-phenyl | |
| 3.023 | H | —CH₂—COOC₂H₅ | |
| 3.024 | methyl | —CH₂—COOCH₃ | |
| 3.025 | isopropyl | —CH₂—CO—NH—C₃H₇(i) | |
| 3.026 | cyclopropyl | —CH₂—CO—N(C₂H₅)₂ | |
| 3.027 | ethyl | —CH₂—CH₂—CN | |
| 3.028 | allyl | —CH₂—CH₂—CN | |
| 3.029 | cyclohexyl | —CH₂—CH₂—CN | |
| 3.030 | phenyl | —CH₂—CH₂—CN | |
| 3.031 | phenyl | —CH₂—CH₂—COOH | |
| 3.032 | cyclohexyl | —CH₂—CH₂—COOCH₃ | m.p. 116–120° |
| 3.033 | 2,6-dimethyl-phenyl | —CH(CH₃)COOCH₃ | m.p. 120–123° |
| 3.034 | phenyl | —CH₂—COOH | |
| 3.035 | phenyl | —CH₂—CN | |
| 3.036 | 4-chlor-phenyl | —CH₂—CN | |
| 3.037 | 2,4-dichlor-phenyl | —CH₂—CN | |
| 3.038 | 3,4-dichlor-phenyl | —CH₂—CN | |
| 3.039 | 3-trifluormethyl-phenyl | —CH₂—CN | |
| 3.040 | methyl | 1-cyanocyclopent-1-yl | m.p. 130–133° |
| 3.041 | | pyrrolidino | |
| 3.042 | | piperidino | |
| 3.043 | | 2-methylpiperidino | |
| 3.044 | | 2-ethylpiperidino | |
| 3.045 | | hexahydroazepino | |
| 3.046 | | morpholino | |
| 3.047 | | 2,2,5,5-tetramethyl 1,3-oxazolidin-3-yl | |
| 3.048 | | 5,5-dimethyl-2,2-tetra-methylen-1,3-oxazolidin-3-yl | |
| 3.049 | | 5,5-dimethyl-2,2-pentamethylen-1,3-oxazolidin-3-yl | |
| 3.050 | | 2-phenyl-1,3-oxazolidin-3-yl | |
| 3.051 | | 2,2-tetramethylen-benzthiazol-3-yl | |
| 3.052 | | 2-oxo-pyrrolidino | |
| 3.053 | | hexahydro-2-oxo-azepino | |
| 3.054 | | 3-oxo-thiomorpholino | |
| 3.055 | | 2-oxo-1,3-oxazolin-3-yl | |
| 3.056 | | 2-trichloromethyl-1,3-oxazolidin-3-yl | |
| 3.057 | H | 2-chlorbenzyl | |
| 3.058 | H | 2-hexylbenzyl | |
| 3.059 | C₂H₅ | C₂H₅ | m.p. 40–41° |
| 3.060 | allyl | H | m.p. 56–58° |
| 3.061 | phenylethyl | H | m.p. 88–89° |
| 3.062 | C₂H₅ | 2,6-dichlorbenzyl | m.p. 89–91° |
| 3.063 | 2-chlorbenzyl | H | m.p. 115–116° |
| 3.064 | allyl | allyl | m.p. 100–101° |
| 3.065 | C₄H₉-n | 2,6-dichlorbenzyl | n_D²⁰ 1.5491 |
| 3.066 | H | ethoxycroton-2-yl | m.p. 72–74° |
| 3.067 | CH(CH₃)₂ | 2-chlorallyl | n_D²⁰ 1.5027 |
| 3.068 | 4-chlor-2-fluor-6-iso-propoxyphenyl | H | m.p. 123–125° |
| 3.069 | cyano-dimethylmethyl | methoxyethyl | m.p. 130–132° |
| 3.070 | chlorphenyl | H | m.p. 125–128° |
| 3.071 | cyano-dimethyl-methyl | H | m.p. 78–80° |

TABLE 3-continued $$CF_3-\underset{N}{\overset{}{=}}\underset{\underset{Cl}{Y}}{\overset{}{=}}-CO-N\underset{R^4}{\overset{R^3}{\diagup}}\qquad(Id)$$

| No. | R₃ | R₄ | phys. constant |
|---|---|---|---|
| 3.072 | 2,2-dimethylindanyl | H | m.p. 174–175° |
| 3.073 | 3,5-bistrifluormethylphenyl | H | m.p. 125–127° |
| 3.074 | diphenylmethyl | H | m.p. 177–179° |
| 3.075 | 2,6-difluorophenyl | H | m.p. 160–161° |
| 3.076 | 5-trifluoromethyl-thiazol-2-yl | H | m.p. 136–138° |
| 3.077 | 2-carboxyl-4-chlorphenyl | H | m.p. 132–134° |
| 3.078 | 3-trifluormethylcyclo-hexyl | H | m.p. 106–109° |
| 3.079 | 2,4,6-trichlorphenyl | H | m.p. 184–186° |
| 3.080 | furfuryl | H | m.p. 100–102° |
| 3.081 | 3,4-methylendioxybenzyl | H | m.p. 129–131° |
| 3.082 | 4-amidosulfonylphenyl | H | m.p. 186–189° |
| 3.083 | 1,2-diphenyleth-1-yl | H | m.p. 146–148° |
| 3.084 | α-methylbenzyl | H | m.p. 131–133° |
| 3.085 | benzoylamido | H | m.p. 192–194° |
| 3.086 | 4-fluorbenzyl | H | m.p. 128–130° |
| 3.087 | 2,2-diphenyleth-1-yl | H | m.p. 127–129° |
| 3.088 | 1-cyano-cyclopent-1-yl | methoxycarbonylmethyl | m.p. 145–147° |
| 3.089 | 1-cyano-cyclohex-1-yl | H | m.p. 145–147° |
| 3.090 | 2-methoxycarbonyl-4-chlorphenyl | H | |
| 3.091 | 1-cyanocyclopent-1-yl | CH₃ | |

TABLE 4

$$CF_3-\underset{N}{\overset{R^3}{=}}\underset{\underset{Cl}{Y}}{\overset{}{=}}-CO-\underset{}{\overset{R^4}{N}}-N(CO)_mR-R^3\qquad(Ie)$$

| No. | —N(R³)—NR³(CO)ₘR⁴ | phys. constant |
|---|---|---|
| 4.001 | —NH—NH₂ | |
| 4.002 | —NH—N(CH₃)₂ | |
| 4.003 | —N(CH₃)—NHCH₃ | |
| 4.004 | —NH—NHphenyl | m.p. 97–99° |
| 4.005 | —NH—NHCOphenyl | |
| 4.006 | —NH—NHSO₂phenyl | |
| 4.007 | —NH—NH(2,4,6-trichlorphenyl) | m.p. 184–186° |
| 4.008 | —NH—NH(2-chlorphenyl) | |
| 4.009 | —NH—NH(4-chlorphenyl) | m.p. 127–130° |
| 4.010 | —N(CH₃)—NHCO(4-chlorphenyl) | |
| 4.011 | —NH—NH(2,4-dichlorphenyl) | m.p. 157–158° |
| 4.012 | —NH—NH(2,6-dichlorphenyl) | m.p. 127–130° |
| 4.013 | —NH—NH(3,5-dichlorphenyl) | m.p. 138–140° |
| 4.014 | —NH-piperidin-1-yl | m.p. 171–173° |

2. Formulation Examples for active ingredients of the formula I (% = percent by weight)

2.1 Wettable powders

| | a) | b) | c) |
|---|---|---|---|
| active ingredient from the Tables 1–3 | 25% | 50% | 75% |
| sodium lignosulphonate | 5% | 5% | — |
| sodium lauryl sulphate | 3% | — | 5% |
| sodium diisobutylnaphthalenesulphonate | — | 6% | 10% |
| octylphenolpolyethylene glycol ether (7–8 mol ethylene oxide) | — | 2% | — |
| highly dispersed silicic acid | 5% | 10% | 10% |
| kaolin | 62% | 27% | — |

The active ingredient is mixed well with the adjuvants and ground well in a suitable mill. Wettable powders are obtained that can be diluted with water to give suspensions of any desired concentration.

2.2 Emulsifiable concentrate

| | |
|---|---|
| active ingredient from the Tables 1–3 | 10% |
| octylphenolpolyethylene glycol ether (4–5 mol ethylene oxide) | 3% |
| calcium dodecylbenzenesulphonate | 3% |
| castor oil polyglycol ether | 4% |

(35 mol of ethylene oxide)
| | |
|---|---|
| cyclohexanone | 30% |
| xylene mixture | 50% |

Emulsions of any desired concentration can be prepared from this concentrate by dilution with water.

2.3 Dusts

| | a) | b) |
|---|---|---|
| active ingredient from the Tables 1–3 | 5% | 8% |
| talcum | 95% | — |
| kaolin | — | 92% |

Dusts that are ready for use are obtained by mixing the active ingredient with the carriers and grinding in a suitable mill.

2.4 Extruder granulate

| | |
|---|---|
| active ingredient from the Tables 1–3 | 10% |
| sodium lignosulphonate | 2% |
| carboxymethylcellulose | 1% |
| kaolin | 87% |

The active ingredient is mixed with the adjuvants, ground and moistened with water. This mixture is extruded and then dried in a stream of air.

2.5 Coated granulate

| | |
|---|---|
| active ingredient from the Tables 1–3 | 3% |
| polyethylene glycol (MW 200) | 3% |
| kaolin | 94% |

(MW = molecular weight)
The finely ground active ingredient is uniformly applied in a mixer to the kaolin moistened with polyethylene glycol. A dust-free coated granulate is obtained in this manner.

2.6 Suspension concentrate

| | |
|---|---|
| active ingredient from the Tables 1–3 | 40% |
| ethylene glycol | 10% |
| nonylphenolpolyethylene glycol ether (15 mol of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants. In this manner, a suspension concentrate is obtained from which suspensions of any desired concentration can be prepared by dilution with water.

3. Biological Examples

Example 3.1

Action against *Puccinia graminis* on wheat a) Residual protective action

Wheat plants are treated 6 days after sowing with a spray mixture (0.06% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

b) Systemic action

Wheat plants are treated 5 days after sowing with a spray mixture (0.02% active ingredient, based on the volume of the soil) prepared from a wettable powder formulation of the test compound. After 48 hours the treated plants are infected with a uredospore suspension of the fungus. The plants are then incubated for 48 hours at 95-100% relative humidity and about 20° C. and then stood in a greenhouse at about 22° C. Evaluation or rust pustule development is made 12 days after infection.

Compounds of the Tables 1-4, especially 1.009, 1.056 und 4.012 exhibit good activity against Puccinia fungi. The Puccinia attack was inhibited almost completely. Puccinia attack is 100% on untreated and infected control plants.

EXAMPLE 3.2

Action against *Cercospora arachidicola* on groundnut plants

Residual protective action

Groundnut plants 10-15 cm in height are sprayed with a spray mixture (0.02% of active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the tables 1-3 is substantially reduced. Thus compound 1.010 inhibits the occurrence of specks almost completely (0 to 10%).

EXAMPLE 3.3

Action against *Erysiphe graminis* on barley a) Residual protection action

Barley plants about 8 cm in height are sprayed with a spray mixture (0.006% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

Compounds of the Tables 1-4 exhibit good activity against Erysiphe fungi. For example, the compounds 1.056, 1.015 inhibited Erysiphe attack almost completely (attack=0-20%). On the other hand, Erysiphe attack is 100% on untreated and infected control plants.

EXAMPLE 3.4

Residual protective action against *Venturia inaequalis* on apple shoots

Residual protective action

Apple cuttings with 10-20 cm long fresh shoots are sprayed with a spray mixture (0.02% a.i.) prepared from a wettable powder formulation of the test compound. The plants are infected 24 hours later with a conidia suspension of the fungus. The plants are then incubated for 5 days at 90-100% relative humidity and stood in a greenhouse for a further 10 days a 20°-24° C. Scab infestation is evaluated 15 days after infection.

Compounds from the Tables 1-4, especially No. 1.010, exhibit good activity against Venturia. Attack is 100% on untreated and infected shoots.

EXAMPLE 3.5

Action against *Botrytis cinerea* on beans

Residual protective action

Bean plants about 10 cm in height are sprayed with a spray mixture (0.02%) prepared from the test compound formulated as a wettable powder. After 48 hours, the treated plants are infected with a conidia suspension of the fungus. The infected plants are incubated for 3 days at 95-100% relative humidity and 21° C., and evaluation of the fungus attack is then made. Some compounds of the Tables 1-4 inhibit fungus attack. At a concentration of 0.02% compound 1.009 e.g. was fully effective (attack 0 to 20%) Botrytis attack on untreated and infected bean plants is 100%.

EXAMPLE 3.6

Action against *Pyricularia oryzae* on rice-plants a) Residual protective action Two week old rice plants are sprayed with a spraying mixture containing 0.006% of active substance, that was prepared from a wettable powder of the substance to be tested. After 48 hours the plants were infested with a suspension containing conidia of the fungus. The infected plants are kept at 24° and 95-100% relative humidity for 5 days before the fungus infestation is evaluated.

b) Systemic action

Two week old rice plants in flower pots are sprayed with a spraying mixture containing 0.006% of active substance, that was prepared by diluting a wettable powder of the substance to be tested with the required amount of water. The flower pots are then added with water so that the stems of the rice plants stand in water. After 48 hours the plants are infected with a suspension containing conidia of the fungus. The fungus-infectation is evaluated after an incubation period of 5 days during which the rice plants were kept at about 24° and 95-100% relative humidity.

The compounds of tables 1 to 4 are very effective against *Pyricularia orizae*. The Pyricularia infection is 100% on infected by not treated control plants. The tested compounds, especially compounds 1.009, 1.115, 1.141, 1.142, 3.040, 4.004, 4.007, 4.009, 4.011, 4.012 and 4.013 inhibited fungus attack on rice plants to 0-5%.

EXAMPLE 3.7

Action against *Tilletia caries* on wheat

Winter barley of the type Probus is infected with spores of *Tilletia caries*, to the rate of 3 g of dry fungus-spore per kg of barley seed. The infected seeds are dried and then macerated in a rolling-mixer with an aqueous solution of the compound to be tested, so that 60 ppm of active substance per weight of seed gets applied. The seeds are then dried. The infected and treated barley is sown in October in a field by means of a sowing machine. Lots of 2 m length containing 3 rows are arranged in triple repetition.

The test is evaluated when the spicules are ripe by evaluating the percentage of spicules infested with *Tilletia caries*.

EXAMPLE 3.8

Action against *Helminthosporium gramineum* on barley

Winter barley of the type "C1" which is naturally infected with *Helminthosporium gamineum* is treated in a rolling-mixer with a solution of the compound to be tested, so that 60 ppm per weight of seed get applied.

The infected and treated barley is sown in October in a field by means of a sowing machine, so that lots of 2 m containing 3 rows of plants are arranged in triple repetition.

The test is evaluated when the spicules develop and the percentage of stalks which are infected with *Helminthosporium gramineum* are counted.

EXAMPLE 3.9

Action against Phytophtora on tomato plants a) Residual-protective action

Three week old tomato-plants are sprayed with a spray-solution containing 0.006% of active substance, which has been prepared from a wettable powder of the substance to be tested. The treated plants are infected with a suspension of sporangia of the fungus. The plants are then kept at 20° and 90-100% relative humidity. The test is evaluated after a 5 day incubation period by evaluation the degree of Phytophthora-infection.

b) Residual-curative action

Three week old tomato-plants are infected with a suspension of sporangia of Phytophthora. After an incubation period of 22 hours in a humid chamber at 20° and 90-100% relative humidity, the infected plants are dried and sprayed with a spray-solution containing 0.006% of active substance.

The tested compounds of tables 1-4 showed in these tests remarkable activity against Phytophtora, especially compounds 1.008, 1.009, 1.012, 1.043, 1.052, 1.095, 1.138, 1.141 and 4.07 showed very good activity.

EXAMPLE 3.10

Action against *Rhizoctonia solani* (soil fungus) on rice plants a) Soil application, local protective action 12 days old rice-plants are watered with a spray-solution, made by dilution of a formulation, containing 0.006% of active substance, in such a manner that none of the plant-parts above ground are contamined. In order to infect the treated plants, a suspension of mycelium and sclerotia of *Rhizoctonia solani* is poured onto the soil around the plant. After 6 days incubation period at 27° temperature (day) and 23° (night) at 100% relative humidity in a humid-box in the clima-room, the fungus infection on the sheath, the leaves and the stem is estimated.

b) Leaf application, local protective action 12 days old rice plants are sprayed with a spray-solution, which has been prepared by diluting a formulation with water. After one day the plants are infected by spraying them with a suspension of mycelium and sclerotia of *Rhizoctonia solani*. After an incubation period of 6 days at a temperature of 27° temperature (day) and 23° (night) at 100% relative humidity in a humid-box in the clima-room, the fungus infection on the sheath, the leaves and the stem is evaluated.

The tested compounds of tables 1, 2 and 4 showed in this test good activity against *Rhizoctoria solani*. Best protection was achieved with compounds No. 1.056 and 3.040.

EXAMPLE 3.11

Action against *Xanthomonas oryzae* on rice (*Oryza sativa*)

a) Residual protective action 3 week old rice plants of the type "Calora" or "S6" are sprayed in the green-house with a spray-solution containing 0.02% of active substance. After one day when the coating from the spray has dried, the plants are put into a clima chamber of 24° temperature and 75-85% relative humidity, where the are infected. Infection is carried out by cutting the points of the leaves with a scissors, which had been dipped into a suspension of *Xanthomonas oryzae*. After 10 days incubation period, the best is evaluated. Infected leaves will curl up and become necrotic. The extent of the pathologic symptoms serves to determine the extent of the residual activity of the substance tested.

b) Systemic action 3 week old rice plants of the type "Calora" or "S6" are sprayed in the green-house with a spray-solution containing 0.006% of active substance. Three days later the plants are put into a clima chamber of 24° temperature and 75-85% relative humidity and infected. Infection is carried out by cutting the points of the leaves with a scissors that has been dipped into a suspension of *Xanthomonas oryzae*. After 10 days incubation period, the test is evaluated. Infected leaves will curl up and become necrotic. The extent of the pathologic symptoms serves to determine the degree of the systemic activity of the substance to be tested.

The tested compounds of tables 1 to 4 showed good activity against *Xanthonomas oryzae*. The compounds 1.010, 1.017, 1.043; 1.066; 1.091; 1.095; 1.113; 1.124; 1.136; 1.137; 1.138; 1.141; 1.142; 4.004; 4.009; 4.011; 4.012 and 4.013 reduced the infection by xanthomonas to 0-20% while infected not treated control plants were 100% infected.

EXAMPLES 3.12

Action against *Colletotrichum lagenarium* on *Cucumis sativus L.* a) After growing for 2 weeks, cucumber plants are sprayed with a spray liquor prepared from a wettable powder of the active substance (concentration: 200 ppm). After 48 hours, the plants are infected with a spore suspension ($1.5 \times 10^5$ spores/ml) of the fungus and incubated at a high atmospheric humidity and a temperature of 23° C. for 36 hours. The incubation is then continued at normal atmospheric humidity and at 22° C. to 23° C.

The protective action is evaluated on the basis of the fungal attack 7-8 days after infection.

b) After growing for 2 weeks, cucumber plants are treated by soil application with a spray liquor prepared from a wettable powder of the active substance (concentration: 60 or 22 ppm, based on the soil volume). After 48 hours, the plants are infected with a spore suspension ($1.5 \times 10^5$ spores/ml) of the fungus and incubated at a high atmospheric humidity and a temperature of 23° C. for 36 hours. The incubation is then continued at normal atmospheric humidity and at 22° C.

The protective action is evaluated on the basis of the fungal attack 7–8 days after infection.

In tests (a) and (b), compounds from Tables 1 to 4 show a good action. Thus, for example compounds 1.015, 1.056, 1.065, 1.121, 1.122, 1.137, 1.138 and 4.007 reduce the fungal attack to 0 to 20%. In contrast, control plants which were untreated but infected show a Colletotrichum attack of 100%.

EXAMPLE 3.13

Action against *Bremia letucae* on lettuce

Lettuce plants two weeks old are watered with a formulated solution of the active substance (0.002% of active substance, based on the soil volume). After 5 days, the treated plants are inocculated with a spore suspension of the fungus ($5 \times 10^4$ spores/ml). The plants are incubated at 18° C. first under a hood (relative atmospheric humidity of 90–100%) for 2 days and then without a hood for 7 days. To bring the fungus to sporulation, the plants are placed under a hood again for 3 days.

The fungal attack is evaluated 12 days after the innoculation on the pasis of the leaf surface attacked by fungus.

Compounds from Tables 1–4 show a good action against Bremia. Thus, plants which were treated with, for example, with compounds No. 1.137, 4.004, 4.009, 4.011, 4.013 and 4.014 remained largely free from attack (0–30% damage). In contrast, plants which were untreated but infected (control) showed a Bremia attack of 100%.

EXAMPLE 3.14

Immunising action against *Pseudomonas lachrymans* on *Cucumis sativus L.*.

a) Foliar application

After a cultivation period of 2 weeks, cucumber plants are sprayed with a sprays mixture (concentration: 0.02% active ingredient) prepared from a wettable powder formulation of the test compound.

After one week the plants are infected with a bacteria suspension ($10^8$ bacteria/ml) and incubated for 7 days at high humidity and at a temperature of 23° C.

Evaluation of the protective action is made 7 to 8 days after infection and is based on the bacteria attack.

b) Soil application

After a cultivation period of 2 weeks, cucumber plants are treated by soil application with a spray mixture (concentration: 0.002% active ingredient, based on the volume of the soil) prepared from a wettable powder formulation of the test compound.

After one week the plants are infected with a bacteria suspension ($10^8$ bacteria/ml) and incubated for 7 days at high humidity and at a temperature of 23° C.

Evaluation of the protective action is made 7 to 8 days after infection and is based on the bacteria attack.

Compounds of Tables 1 to 4 result in good immunisation against *Pseudomonas lachrymans*. Thus, plants treated e.g. with compounds No. 1.065, 1.137, 4.004, 4.007, 4.009, 4.011 and 4.012 remain virtually completely free of Pseudomonas (20 to 0% attack).

Untreated and infected control plants exhibit 100% attack of the disease in tests A and B.

EXAMPLE 3.15

Action against *Xanthomonas vesicatoria* on paprika plants a) Foliar application After a cultivation period of 4 weeks, paprika plants are treated by foliar application with a spray mixture (concentration: 0.02% active substance) prepared from a wettable powder formulation of the test compound. After 2–3 days the plants are inoculated with a bacteria suspension ($10^8$ bacteria/ml) and incubated for 6 days at high humidity and at a temperature of 25° C. Evaluation of the protective action is made 7–8 days after inoculation and is based on the bacteria attack.

Untreated and infected control plants exhibit 100% attack in this test.

b) Soil application

After a cultivation period of 4 weeks, paprika plants are treated by soil application with a spray mixture (concentration: 0.006% based on the volume of the soil) prepared from a wettable powder formulation of the test compound. After 2–3 days the plants are inoculated with a bacteria suspension ($10^8$ bacteria/ml) and incubated for 6 days at high humidity and at a temperature of 25° C.

Evaluation of the protective action is made 7–8 days after inoculation and is based on the bacteria attack.

Untreated and infected control plants exhibit 100% attack in this test.

Compounds of Tables 1 to 4 show good activity against *Xanthomonas vesicatoria*. Thus, plants treated e.g. with compounds No. 1.010, 1.091, 1.095, 1.137, 1.142 and 4.007 remain virtually completely free of *Xanthomonas vesicatoria* (20 to 0% attack).

EXAMPLE 3.16

Action against *Erysiphe graminis* on wheat a) Protective Action

17 Days old wheat plants are treated with a formulated spraying solution containing 0.02% of active substance. Immediately after spraying the plants were incubated under cylinders. The cylinders were taken away after 24 hours and the plants left in the open for 3 days. Then the plants were cut off above the primary leaf. The primary leaves were then brought to a horizontal position and the plants were infested with an aqueous suspension, so that 0.2 mg of *Erysiphe graminis* spores got distributed per m². The infested plants were then left to develop in a climatic chamber under conditions of 12 hours daylight of 18 000 Lux at 20° C. temperature and 12 hours dark at 18° C. temperature.

The test was evaluated 9 and 12 days after inoculation by measuring degree of infestation.

The compounds of tables 1–4 show good activity against *Erysiphe graminis*. The plants that were treated with compounds No. 1.137, 4.004, 4.007, 4.009, 4.011 and 4.012 remained practically free from infestation (0–20% infestation), while untreated but inoculated control plants showed infestation by *Erysiphe graminis* of 100%.

We claim:

1. An agricultural method which comprises inhibiting the growth of phytopathogenic microorganisms on a cultivated plant or curing a cultivated plant which is infested with phytopathogenic microorganisms by treating the plant, seed or locus of the plant with a microbicidally effective amount of a 2-chloro-4-trifluoromethyl-thiazol-5-carboxylic acid derivative of the formula Ia

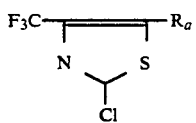

wherein $R_a$ is a radical —$COXR_1$.

X is oxygen or sulfur, $R_1$ is hydrogen; $C_1$–$C_{18}$alkyl, which is unsubstituted or substituted by halogen, a cyano group, nitro, —$YR_2$, A, —$N(R_3)COA$, D, —$[N(R_3)]_m$—$CON[(CO)_m$—$R_3]_m$—$(CO)_mR_4$ in which group one of the indices m must be zero, —$C(X)_mXR_7$, —$(X)_m$—$CXA$, —$PO(R_5)R_6$, $C_3$–$C_8$cycloalkyl or $C_5$–$C_8$cycloalkenyl, which is unsubstituted or substituted by halogen, $C_1$–$C_4$alkyl or methylenedioxy; $R_1$ further represents $C_3$–$C_8$-alkenyl, $C_3$–$C_{18}$cycloalkyl or $C_3$–$C_{18}$cycloalkenyl, which is unsubstituted or substituted by halogen, $C_1$–$C_4$alkoxy, $C_1$–$C_4$alkylthio, $C_1$–$C_4$haloalkoxy, $C_1$–$C_4$haloalkyl, methylenedioxy or —$CO(O)_m$—$R_7$, —COA, or —$PO(R_5)R_6$; $R_1$ further represents $C_3$–$C_8$alkynyl which is unsubstituted or substituted by halogen or represents —$(E)_mU$ or —$(E)_mQ$, $R_2$ is $C_1$–$C_8$alkyl or $C_3$–$C_8$cycloalkyl, which is unsubstituted or substituted by $C_1$–$C_8$alkoxy, $C_1$–$C_8$alkylthio, $C_2$–$C_8$alkoxyalkyl halogen, cyano or —$CX(X)_mR_7$, —$(X)_m$—$CXA$, —$(X)_mCXR_7$, —$N(R_3)COA$, A, —$X$—$U$ or XQ; $R_2$ further represents $C_3$–$C_8$alkenyl or $C_3$–$C_8$cycloalkenyl, which is unsubstituted or substituted by halogen or represents —$(E)_mU$ or —$(E)_mQ$;

m is zero or one;

Y is oxygen, sulfur, SO or $SO_2$;

A is a radical —$N(R_3)R_4$;

D is a radical —$N(R_3)N(R_4)(CO)_mR_3$;

$R_3$ and $R_4$ independently of each other represent hydrogen, $C_1$–$C_8$alkyl or $C_3$–$C_8$cycloalkyl, which is unsubstituted or substituted by $C_1$–$C_8$alkoxy, $C_2$–$C_8$alkoxyalkoxy, $C_1$–$C_8$alkylthio, cyano, —$COOR_{10}$, $C_1$–$C_4$alkylcarbamoyl, di-$C_1$–$C_4$alkylcarbamoyl, piperidinocarbonyl, pyrrolidinocarbonyl, piperidino or pyrrolidino; $R_3$ and $R_4$ further represent $C_3$–$C_8$alkenyl or $C_3$–$C_8$cycloalkenyl which is unsubstituted or substituted by halogen, $C_1$–$C_8$alkoxy, $C_3$–$C_8$cycloalkyl or cyano, —$COOR_7$, $C_1$–$C_4$alkylcarbamoyl or piperidinocarbamoyl; $R_3$ and $R_4$ represent further $C_3$–$C_8$alkynyl, which is unsubstituted or substituted by U, or $R_3$ and $R_4$ represent a radical —$(E)_mU$ or —$(E)_mQ$;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$–$C_8$alkoxy, amino, $C_1$–$C_4$alkylamino di-$C_1$–$C_4$alkylamino or —$COOR_7$;

$R_5$ and $R_6$ are independently of each other are hydrogen or $C_1$–$C_4$alkoxy;

$R_7$ is hydrogen, $C_1$–$C_8$alkyl, $C_3$–$C_8$cycloalkyl, $C_3$–$C_8$alkenyl, $C_2$–$C_8$alkoxyalkyl, $C_3$–$C_8$alkoxyalkoxyalkyl, $C_1$–$C_4$haloalkyl, —$(C_1$–$C_3$alkylene)_mU$, —$(C_1$–$C_3$alkylene)_mQ$, $C_1$–$C_4$haloalkoxy;

U is phenyl or naphthyl, which is unsubstituted or substituted one to three times by halogen $C_1$–$C_4$alkyl, —Y—$C_1$–$C_4$alkyl, $C_1$–$C_4$haloalkyl, $C_1$–$C_4$haloalkoxy, cyano, nitro, carboxyl, —$COOR_7$, —$CONH_2$, —$CONHR_7$, —$CON(R_7)$, —$SO_2NHR_7$, —$SO_2N(R_7)_2$, pyrrolidino, piperidino, pyrrolidino, carbonyl or piperidinocarbonyl;

E is a $C_1$–$C_8$alkylene or $C_2$–$C_8$alkylene chain, which is unsubstituted or substituted by halogen, $C_1$–$C_4$alkoxy, $C_1$–$C_4$alkylthio, $C_1$–$C_4$haloalkoxy or by a group —$CO(O)_mR_7$, —$(CO)_mA$ —$(CO)_mQ$;

Q is a heterocycle which is bound via a carbon atom and is selected from among furan, tetrahydrofuran pyran, pentahydropyran, dioxolan, dioxan, benzdioxan, dihydrobenzdioxan, thienyl, thiazol, which may be substituted by halogen or methyl.

2. A method of claim 1 wherein X is O.

3. A method of claim 1 wherein the 2-chloro-4-trifluoromethyl-thiazol-5-carboxylic acid derivative is selected from the group consisting of 2-chloro-4-trifluoromethyl-thiazol-5-carboxylic acid, 2-chloro-4-trifluoromethyl-thiazol-5-carboxylic acid-benzyl ester, 2-chloro-4-trifluoromethyl-thiazol-5-carboxylic acid-ethyl ester, 2-chloro-4-trifluoromethyl-thiazol-5-carboxylic acid-(2-cyanoethyl)ester, 2-chloro-4-trifluoromethyl-thiazol-5-carboxylic acid-(2-phenoxyethyl)ester, 2-chloro-4-trifluoromethyl-thiazol-5-carboxylic acid-(2-phenylthioethyl)ester, 2-chloro-4-trifluoromethyl-thiazol-5-carboxylic acid-(diphenylmethyl)ester, 2-chloro-4-trifluoromethyl-thiazol-5-carboxylic acid-($\alpha$-cyanobenzyl)ester, 2-chloro-4-trifluoromethyl-thiazol-5-carboxylic acid-($\alpha$-benzoyl-benzyl)ester, 2-chloro-4-trifluoromethyl-thiazol-5-carboxylic acid-(2-methylsulfonyl-ethyl)ester, 2-chloro-4-trifluoromethyl-thiazol-5-carboxylic acid-(2,3,5,6-diepoxycyclohexan-1-yl)ester, 2-chloro-4-trifluoromethyl-thiazol-5-carboxylic acid-(2,2-dimethyl-1,3-dioxolan-2-yl-methyl)ester, 2-chloro-4-trifluoromethyl-thiazol-5-carboxylic acid-azepinomethylester, 2-chloro-4-trifluoromethyl-thiazol-5-carboxylic acid-(piperidinoeth-1-yl)-ester, 2-chloro-4-trifluoromethyl-thiazol-5-carboxylic acid-[2-(4-methylthiazol-5-yl)ethyl]ester, 2-chloro-4-trifluoromethyl-thiazol-5-carboxylic acid-[2-(5-methylthiazol-4-yl)ethyl]ester, 2-chloro-4-trifluoromethyl-thiazol-5-carboxylic acid-[2-piperidinocarbonyl-ethyl)ester, 2-chloro-4-trifluoromethyl-thiazol-5-carboxylic acid-(piperidinocarbonyl-eth-1-yl)ester.

4. A method of claim 1 wherein the 2-chloro-4-trifluoromethyl-thiazol-5-carboxylic acid derivative is of the formula Ic

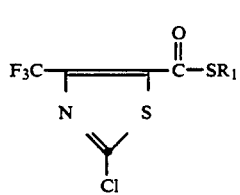

wherein $R_1$ is $C_1$–$C_{18}$alkyl or $C_3$–$C_{18}$cycloalkyl unsubstituted or $C_1$–$C_{18}$-alkyl substituted by halogen $C_1$–$C_8$alkoxy, $C_1$–$C_8$alkylthio, $C_2$–$C_8$alkoxyalkoxy nitro, cyano or A—, $CX(X)_mR_7$, —$N(R_3)COA$, A is —N($R_3$)$R_4$ or —(E)$_m$U m is zero or one $R_3$ and $R_4$ independently of each other are hydrogen, $C_1$-$C_8$alkyl, $C_3$-$C_8$-alkenyl or —(E)$_m$—U or $R_3$ and $R_4$ together with the nitrogen atom to which they are bound form a heterocycle selected from the group consisting of pyrrolidine, piperidine, azepine and morpholine $R_7$ is hydrogen or $C_1$-$C_{10}$alkyl E is $C_1$-$C_8$alkylene or $C_2$-$C_8$alkenylene chain U is phenyl or naphthyl, which is unsubstituted or substituted by halogen, $C_1$-$C_4$alkoxy or —CO(O)$_m$$R_7$, and X is oxygen or sulfur.

5. A method of claim 1 wherein the cultivated plant is selected form the group consisting of beets, pomes, drupes and soft fruits, leguminous plants, oil plants, cucumber plants, fiber plants, vegetables, lauraceae, ornamentals, tobacco, nuts, coffee, sugar cane, tea, vines, hops, bananas and natural rubber plants.

6. A method of claim 1 wherein the cultivated plant is a cereal selected from the group consisting of wheat, barley, rye and oats.

7. A method according to claim 1 wherein the microorganisms are phytophatogenic fungi or soil borne phytopathogenic bacteria.

8. A method according to claim 1 which comprises treating seeds.

9. A method according to claim 1 which comprises treating rice plants.

10. A method of claim 1 wherein a cultivated plant, which is infested with phytopathogenic microorganism, is cured.

* * * * *